United States Patent
Pennig

Patent Number: 5,375,956
Date of Patent: Dec. 27, 1994

[54] HEAD SCREW CONSTRUCTION FOR USE IN FIXING THE POSITION OF AN INTRAMEDULLARY NAIL

[76] Inventor: Dietmar Pennig, Hans-Driesch-Strasse 12, 50935, Cologne, Germany

[21] Appl. No.: 171,274

[22] Filed: Dec. 21, 1993

[30] Foreign Application Priority Data

Mar. 11, 1993 [DE] Germany .............. 4307633

[51] Int. Cl.⁵ .............. F16B 35/00; F16B 35/04; A61F 5/04
[52] U.S. Cl. .............. 411/389; 411/397; 411/410; 411/413; 606/65; 606/73
[58] Field of Search .............. 411/374, 389, 397, 410, 411/412, 413; 606/65, 66, 73

[56] References Cited

U.S. PATENT DOCUMENTS

| | | | |
|---|---|---|---|
| 3,741,205 | 6/1973 | Markolf et al. | 606/73 X |
| 4,463,753 | 8/1984 | Gustilo | 411/412 X |
| 4,723,541 | 2/1988 | Reese | |
| 4,764,069 | 8/1988 | Reinwall et al. | 411/397 |
| 4,854,311 | 8/1988 | Steffee | 411/389 |
| 5,019,079 | 5/1991 | Ross | 411/389 X |
| 5,032,125 | 7/1991 | Durham et al. | 606/73 X |
| 5,116,337 | 5/1992 | Johnson | |

FOREIGN PATENT DOCUMENTS

| | | |
|---|---|---|
| 2246274 | 9/1972 | Germany . |
| 0306709 | 3/1989 | European . |

*Primary Examiner*—Neill R. Wilson
*Attorney, Agent, or Firm*—Hopgood, Calimafde, Kalil & Judlowe

[57] ABSTRACT

The invention relates to a screw for fixing an intramedullary nail in position. An external thread on the screw shank is provided over only a part of the length of the shank. The screw head is provided with an external thread having a direction of helical advance which is opposite the direction of helical advance of the screwshank thread.

12 Claims, 1 Drawing Sheet

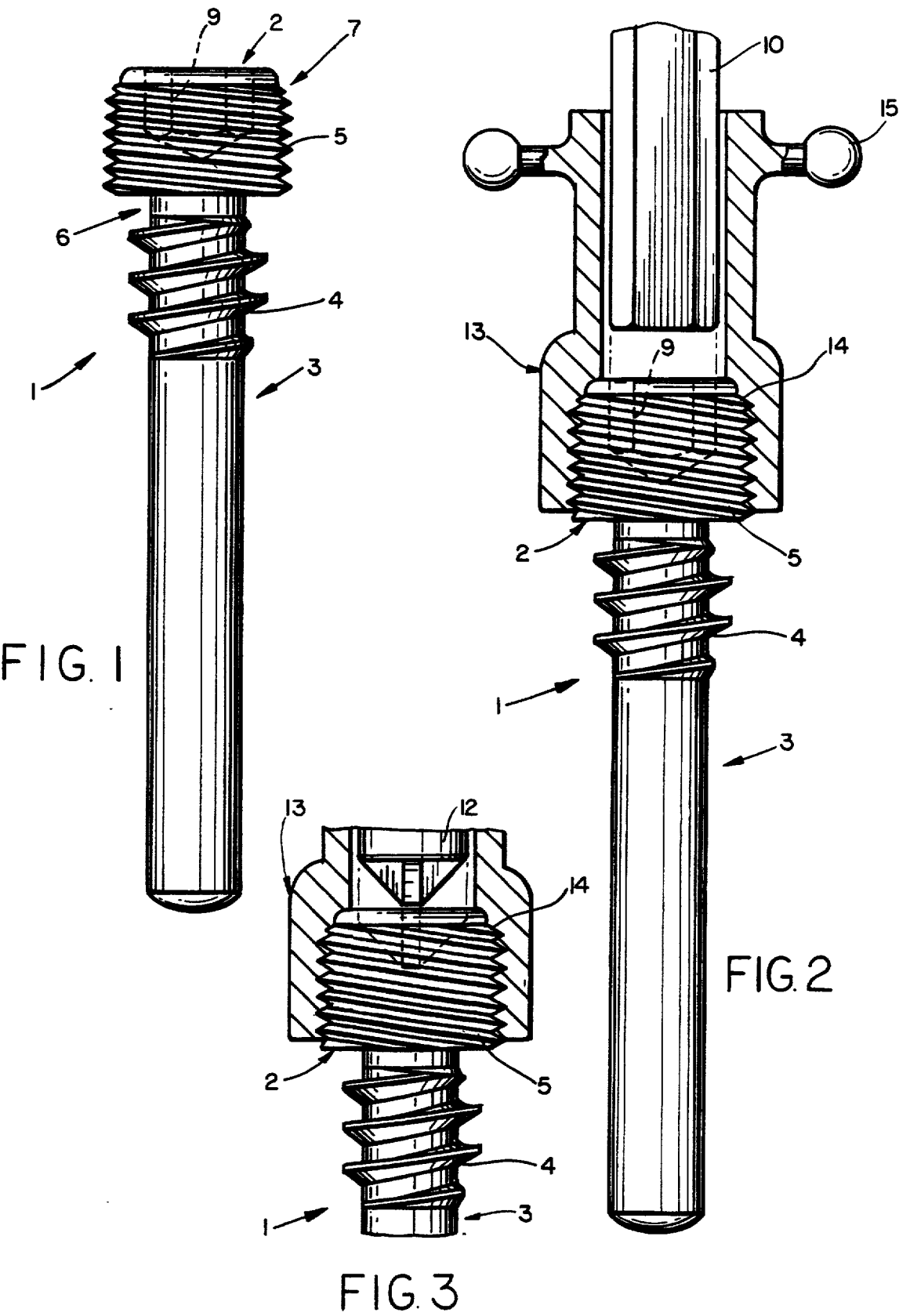

HEAD SCREW CONSTRUCTION FOR USE IN FIXING THE POSITION OF AN INTRAMEDULLARY NAIL

BACKGROUND OF THE INVENTION

The present invention relates to a headed screw construction wherein the shank of the screw locates in transverse anchor holes of an intramedullary nail and wherein threads on the shank of the screw are adapted for anchorage in bone.

The use of screw threads to fix or to anchor an intramedullary nail is known from EP 306,709 A2. In that case, an elongate screw is threaded for the entire length of its shank and passes through the intramedullary nail.

Screws having a shank with external threads only over a part of their length are known from U.S. Pat. No. 4,463,753. In that case, the two spaced regions of screw threads on the same shank serve to provide a compressive action, bringing together two fracture-separated parts of a bone. Threaded advance for the respective spaced thread regions is in the same direction, but with differing pitch. This prior art screw has no relation to an intramedullary nail.

BRIEF STATEMENT OF THE INVENTION

The object of the present invention is to provide a screw construction for fixing the position of an intramedullary nail, wherein the screw is easily positioned for intramedullary-nail engagement and is easily removable.

The invention achieves this object in a screw construction (a) in which threads for engagement in bone are limited to the shank region near the headed end of the screw, (b) in which the remainder of the shank, i.e., beyond the threads, is unthreaded, and (c) in which the head itself is externally threaded with a direction of thread advance that is opposite to the direction of thread advance on the shank. The unthreaded part of the screw shank is intended for passage through the intramedullary nail, while the threaded region of the shank secures the screw in cortical substance of a bone. Later on, when the screw is to be removed from its threaded anchorage to bone, an internally threaded nut may be threaded onto the external threads of the head. Once the nut has achieved a limit of head-thread engagement, continued nut rotation in the same direction is operative to drive the shank threads to retract the same from bone engagement. Thus, the screw of the invention can be removed from pinned locating engagement with the intramedullary nail and from threaded engagement to a bone, merely by driving the nut in the direction opposite to the direction of initial shank-screw engagement to the bone.

Admittedly, the retracting direction of screw rotation could also be obtained using an Allen-head wrench, but an Allen-head wrench does not enable a retracting pull to be exerted on the screw. Thus, it is practically impossible to use an Allen-head wrench or a Phillips screwdriver to detach an ingrown screw from bone. The external thread on the screw head does not start at the top of the screw head but, rather, offset somewhat from the top of the screw head. There is therefore a cylindrical feature in the region of the screw head, to facilitate attachment of the internally threaded nut.

Between the bottom of the screw head and the external thread on the screw shank, there is a free space the size of which depends on the size of the screw and the purpose of its use.

An embodiment of the invention will be described in detail, in conjunction with the accompanying drawings, in which:

BRIEF DESCRIPTION OF THE DRAWINGS

FIG. 1 is an enlarged view in side elevation of a headed-screw construction of the invention;

FIG. 2 is a fragmentary view similar to FIG. 1, to show tool-engagement to the headed screw of FIG. 1; and FIG. 3 is a view similar to FIG. 2 to show another tool engagement for a modified screw-head construction.

DETAILED DESCRIPTION OF THE INVENTION

In FIG. 1, a screw 1 of the invention is shown to have a head 2 and a shank 3. The greater part of the screw shank is unthreaded and smoothly cylindrical, and a screw-shank thread 4 is provided only in the vicinity of the bottom of the screw head 2. When using screw 1 to fix the position of an intramedullary nail, this screw-shank thread 4 is thread-engaged in cortical substance of the bone.

The screw head 2 is shown with a polygonal key or socket formation 9, as for driving engagement by an Allen-head wrench 10 (FIG. 2). But the screw head 2 may be otherwise key-formed, as at 11 for driving engagement by a Phillips screwdriver 12 (FIG. 3); thus, the screw 1 may be formed for inwardly driven engagement to bone, merely by selection of a suitable wrench or screwdriver.

The outside of the screw head 2 is provided with a screw-head thread 5, the thread-advance of which is directed opposite the direction of thread-advance of the screw-shank thread 4, i.e., one of these threads is a right-hand thread, and the other is a left-hand thread. This being the case, an internally threaded tool such as a nut 13 may be threaded onto the head thread 5, to the point of engagement with a stop, such as an internal shoulder formation 14; once the stop 14 is engaged, continued nut rotation in the same direction is operative to retract screw 1 from the patient's bone. And, if perchance, the threaded shank-to-bone engagement has been so fretted as to make unthreading retraction impossible, the nut 13 will serve as a readily grasped means of directly pulling the screw out of its inadequate engagement to the bone.

As shown in the drawing, a short cylindrical unthreaded formation 7 provides a crown or chamfer between the upper end of the screw-head thread 5 and the top of the screw head 2; this formation 7 facilitates location of nut 13 on the screw-head thread 5 even though the screw head 2 may be immersed within the patient's flesh and is therefore not visible. Preferably, the axial extent of formation 7 is at least one full turn of the internal thread of nut 13. And suitably, nut 13 has external formations 15 to facilitate manual grasping, in the course of a retraction of screw 1 from the patient.

Another unthreaded region 6 may also be provided between the bottom of the screw head 2 and the screw-head thread 4, said region 6 depending on the size of the screw and on the purpose of use.

What is claimed is:

1. A headed screw (1) with a bone-engaging screw thread, comprising an elongate shank (3) having an external thread (4) for bone-engaged anchorage of said screw (1), and a drive head (2) at one end of said shank (3), wherein:
- (a) the shank thread (4) is close to said head (2) and extends for only a portion of the length of said shank (3);
- (b) the head (2) has a key formation that is externally accessible for selective rotation of the headed screw (1) in a first direction of advancing screw-thread engagement in bone; and
- (c) the head (2) has an external thread (5) having a direction of thread advance which is opposite to the direction of shank-thread (4) advance.

2. The headed screw of claim 1, in which said key formation is a concave polygonal socket that is adapted for rotary drive via a convex polygonal tool.

3. The headed screw of claim 1, in which said key formation is a concave cruciform socket that is adapted for rotary drive via a convex cruciform tool.

4. The headed screw of claim 2, in which the polygonal tool is an Allen-head wrench.

5. The headed screw of claim 3, in which said convex cruciform tool is a Phillips-head screwdriver.

6. The headed screw of claim 1, in which the pin shank (3) has a free unthreaded end extending away from the shank thread (4) in the direction that is away from said head (2), the shank thread being at longitudinal offset from said free unthreaded end.

7. The headed screw of claim 1, in which the root diameter of the head thread (5) is also approximately the external diameter of the shank thread (4).

8. The headed screw of claim 6, in which the axial length of the free unthreaded end of the shank is greater than the axial length of the shank thread (4).

9. The headed screw of claim 6, in which the external diameter of the shank thread (4) decreases in approach to the free unthreaded end.

10. In combination, the headed screw of claim 1, and a nut having an internally threaded bore adapted for removable engagement to the external thread (5) of said head, said threaded bore terminating at an internal stop, whereby nut rotation in the direction to advance said nut on the thread of said head to the point of internal-stop engagement will, on continued rotation in the same direction, thereafter drive the medullary pin in the direction of unthreading retraction from engaged bone.

11. In combination the headed screw of claim 2, and a nut having an internally threaded bore that is open at one axial end of the nut and at least partially closed at the other axial end of the nut, said internally threaded bore being adapted for removable engagement to the external thread (5) of said head, and the at least partially closed portion of the bore establishing an internal stop against further threaded advance of the thread (5) of said head into the bore of said nut, whereby nut rotation in the direction to advance said nut on the thread of said head to the point of internal-stop engagement will, on continued rotation in the same direction, thereafter drive the medullary pin in the direction of unthreading retraction from engaged bone.

12. The combination of claim 11, in which, at its axially outer end, said head has a key formation, and the partial closure of said nut establishes a circular rim of diameter to clear an inserted key-engaging tool into head engagement with said key formation.

* * * * *

UNITED STATES PATENT AND TRADEMARK OFFICE
CERTIFICATE OF CORRECTION

PATENT NO.  : 5,375,956
DATED       : December 24, 1994
INVENTOR(S) : DIETMAR PENNIG It is certified that error appears in the above-identified patent and that said Letters Patent is hereby corrected as shown below:

On the title page item [54], should read:

-- HEADED SCREW CONSTRUCTION FOR USE IN FIXING
   THE POSITION OF AN INTRAMEDULLARY NAIL       --

Signed and Sealed this

Fourteenth Day of March, 1995

*Attest:*

Bruce Lehman

BRUCE LEHMAN

*Attesting Officer*   *Commissioner of Patents and Trademarks*